United States Patent [19]

Bru-Magniez et al.

[11] Patent Number: 4,595,686
[45] Date of Patent: Jun. 17, 1986

[54] NIFLUMIC ACID MORPHOLINOETHYL ESTER DINIFLUMATE, USE AS ANALGESIC AND ANTI-INFLAMMATORY AGENTS AND COMPOSITIONS

[75] Inventors: Nicole Bru-Magniez, Paris; Jean-Marie Teulon, La Celle St Cloud; Romano Deghenghi, Le Pecq, all of France

[73] Assignee: Hexachimie, Rueil-Malmaison, France

[21] Appl. No.: 597,808

[22] Filed: Apr. 9, 1984

[30] Foreign Application Priority Data

Apr. 21, 1983 [FR] France ................ 83 06579

[51] Int. Cl.[4] ................ A61K 31/535; C07D 295/14
[52] U.S. Cl. ................ 514/236; 544/131
[58] Field of Search ................ 544/131; 514/236

[56] References Cited

U.S. PATENT DOCUMENTS

| Re. 27,822 | 11/1973 | Koppe et al. ................ 260/501.1 |
| 3,708,481 | 1/1973 | Hoffman ................ 544/131 |
| 4,370,489 | 1/1983 | Boesenberg et al. ................ 560/62 |
| 4,386,090 | 5/1983 | Moinet et al. ................ 424/248.4 |

FOREIGN PATENT DOCUMENTS 858349 9/1977 Belgium .
1146459 3/1969 United Kingdom .

OTHER PUBLICATIONS

*The Merck Index*, 9th Ed. (1976), No. 6355.

*Primary Examiner*—Robert Ramsuer
*Attorney, Agent, or Firm*—Lowe Price Leblanc Becker & Shur

[57] ABSTRACT

A novel compound of formula:

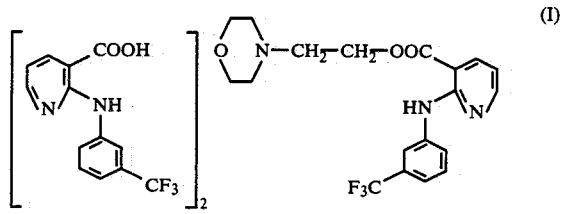

useful as analgesic and anti-inflammatory drug, with very interesting therapeutic index.

4 Claims, No Drawings

NIFLUMIC ACID MORPHOLINOETHYL ESTER DINIFLUMATE, USE AS ANALGESIC AND ANTI-INFLAMMATORY AGENTS AND COMPOSITIONS

The present invention relates to niflumic acid β-morpholinoethyl ester diniflumate, of formula I, to the preparation thereof and to its therapeutical applications:

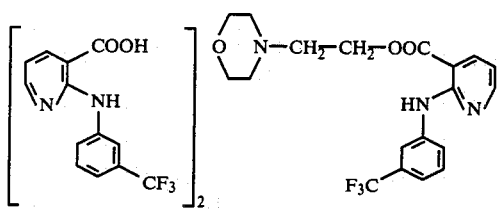

This novel product of formula I according to the invention is endowed with interesting pharmacological activities, offering numerous advantages over the known drug, niflumic acid, as may be ascertained on reading the Patent, and may be useful in therapeutics, particularly as analgesic and anti-inflammatory agent.

This product, well defined in stable crystalline form, having a well characterized melting point, is formed between two molecules of niflumic acid and one molecule of the β-morpholinoethyl ester of niflumic acid.

It is known that niflumic acid is the ICD of 2-(3-trifluoromethyl phenylamino) nicotinic acid and amino ester is β-morpholinoethyl 2-(3-trifluoromethyl phenylamino) nicotinate (also called morniflumate).

Niflumic acid is a well known drug described in French Special Drug Pat. No. 4 267 M filed on Dec. 9, 1964.

The product according to the invention may be prepared by action of β-morpholinoethyl 2-(3-trifluoromethyl phenylamino) nicotinate on double the stoichiometric quantity of the 2-(3-trifluoromethyl phenylamino) nicotinic acid in an appropriate solvent.

The invention will be illustrated by the following non-limiting Examples.

EXAMPLE 1

To a solution of 99 g of β-morpholinoethyl 2-(3-trifluoromethyl phenylamino) nicotinate (0.25 mole) in 1 l of ethyl ether, is added a solution of 141 g of 2-(3-trifluoromethyl phenylamino) nicotinic acid (0.5 mole) in 1 l of ethyl ether. The solution thus obtained is filtered. The ethyl ether is evaporated and the residue obtained crystallizes. By taking up these crystals, hot, in isopropyl ether, then by cooling, 218 g of niflumic acid morpholinoethyl ester diniflumate are obtained, after draining and draining and drying, in the form of pale yellow crystals with a melting point (non-corrected capillary) of 109° C. Yield: 91%

EXAMPLE 2

A mixture of 19.8 g of β-morpholinoethyl 2-(3-trifluoromethyl phenylamino) nicotinate (0.05 mole) and 28.2 g of 2-(3-trifluoromethyl phenylamino) nicotinic acid (0.1 mole) is dissolved in 175 ml of acetone. The solution is filtered then the filtrate is concentrated in vacuo, the residue obtained, which crystallizes, is taken up in 500 ml of isopropyl ether, hot. After cooling, the crystals are drained and dried. 45.6 g of niflumic acid morpholinoethyl ester diniflumate are thus recovered in the form of pale yellow crystals, with a melting point (non-corrected capillary) of 109° C. Yield: 95%

EXAMPLE 3

A mixture of 19.8 g of β-morpholinoethyl 2-(3-trifluoromethyl phenylamino) nocitinate (0.05 mole) and 28.2 g of 2-(3-trifluoromethyl phenylamino) nicotinic acid (0.1 mole) is dissolved in 175 ml of methanol between 40° and 45° C. After filtration, the solution is evaporated in vacuo and the residue obtained crystallizes. The crystals are taken up, hot, in 250 ml of isopropyl ether, then, after having cooled, the crystals are drained, then dried. 46 g of niflumic acid morpholinoethyl ester diniflumate are thus obtained in the form of pale yellow crystals with a melting point (non-corrected capillary) of 109° C. Yield: 95.8%.

The anti-inflammatory, analgesic and ulcerogenic activities of the product of formula I have been assessed at the same time as those of niflumic acid.

The results show that, on molar bases, the product of formula I is from 2 to 3 times more active than niflumic acid on the inflammation and analgesia tests. On the other hand, the product of formula I is only 1.5 times more ulcerogenic than niflumic acid.

This set of results is surprising.

The following Table groups together the median active doses ($AD_{50}$) and median ulcerogenic doses ($UD_{50}$) expressed in μM/kg VO. The pharmacological index corresponds to the ratio:

| $AD_{50}$ oedema/$UD_{50}$ | | |
| --- | --- | --- |
| | Product of formula I invention | niflumic acid |
| Oedema by carragenin | 50.2 | 111.7 |
| Torsions by P.B.Q.* | 61.0 | 152.4 |
| Ulcerogenic action (fasting rats) | 30.2 | 46.0 |
| Pharmacological index | 1.66 | 2.43 |

*Phenylbenzoquinone

The above tests were carried out in accordance with the techniques described hereinafter.

Anti-inflammatory action

It was assessed on the oedema by carragenin.

Technique

A modification of the method of Winter et Coll. (1962) was employed.

Batches of 12 male rats of CD (Charles River) strain, weighing 120–150 g, receive for food and drink an aqueous solution with 9% of sodium chloride and 15% of glucose, 18 hours before the test.

The product under study is administered by the oral route on two occasions in a total volume of 5 ml. 100 $g^{-1}$: a half-dose 2 hours and a half-dose 30 minutes before sub-cutaneous injection in the plantar pad of a rear paw of 0.05 ml of a 1.5% aqueous solution of carragenin. The volume of the paw is measured by plethysmography (Ugo Basile plethysmograph), at regular intervals for 4 hrs. 30 mins.

The above Table gives the percentage of inhibition of the reaction.

Analgesic activity

Antagonism of phenylbenzoquinone (torsions by P.B.Q.)

Technique

The analgesic action is studied by the technique of SIEGMUND et coll. (1957).

Batches of 12 male mice, of CD 1 (Charles River) strain, weighing 19-22 g, receive by the intraperitoneal route 0.25 ml of a 0.02% dilute alcoholic solution of phenylbenzoquinone, one hour after administration by the oral route of the product under study (0.5 ml. $20^{-1}$).

The number of painful reactions (torsions, stretchings) from the 5th to the 10th minute are counted.

The above Table gives the percentage of inhibition of the reactions with respect to controls.

Ulcerogenic action

Technique

Batches of 8 to 14 male rats of OFA (Iffa Credo) strain, weighing 110-140 g, are placed on a diet of water 24 hours before oral administration of the product under study, in a volume of 2 ml. 100 $g^{-1}$.

The animals are sacrificed 6 hours after the treatment; the stomachs are removed, incised along the large curvature then marked from 0 to 3 according to the scale described by L WOFF (1971):

0: no ulcers
1: 1 to 2 ulcers
2: 3 to 4 ulcers
3: more than 4 ulcers

The average of the results for one batch, multiplied by the percentage of rats presenting ulcers in this batch, gives an index of ulceration of which the maximum is 300.

The Table gives the indices of ulceration per batch. The median ulcerogenic dose ($UD_{50}$) is indicated in $\mu M/kg$.

Conclusions

The anti-inflammatory and analgesic effects of the morniflumate diniflumate, of formula I, were assessed with respect to the oedema by carragenin and the test of torisons by phenylbenzoquinone. The ulcerogenic effect was sought in the fasting rat.

The results obtained show that:

morniflumate diniflumate is 2.2 times more active than niflumic acid on the acute inflammation test;
its analgesic effect is 2.5 times greater than that of niflumic acid;
it is 1.5 times more ulcerogenic than niflumic acid.

The pharmacological index is clearly greater for the salt of formula I with respect to niflumic acid.

The product of formula I may essentially be formulated as tablets, capsules, suppositories, rectal capsules, solutes, gels and ointments for therapeutic use, at doses of 1 to 10 mg/kg of body weight.

What is claimed is:

1. A compound consisting of niflumic acid morpholinoethyl ester diniflumate of formula:

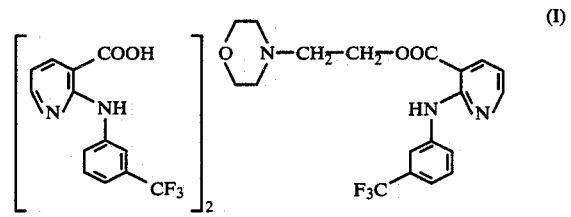

2. An anti-inflammatory and analgesic pharmaceutical composition comprising an effective amount of the compound of claim 1 and a pharmaceutical carrier.

3. A method for the treatment of inflammation in mammals which comprises the administration of the anti-inflammatory composition of claim 2 at a dosage amount of 1-10 mg/kg of body weight.

4. A method for the treatment of analgesia in mammals which comprises administering the pharmaceutical composition of claim 2 in an amount of 1-10 mg/kg of body weight.

* * * * *